US011371092B2

(12) United States Patent
Gordon et al.

(10) Patent No.: US 11,371,092 B2
(45) Date of Patent: Jun. 28, 2022

(54) DETECTION DEVICE AND METHODS OF USE

(71) Applicant: QIAGEN SCIENCES, LLC, Germantown, MD (US)

(72) Inventors: Steven Gordon, Weston, MA (US); Steven Auger, Cohasset, MA (US); Alan Schinazi, Providence, RI (US)

(73) Assignee: QIAGEN SCIENCES, LLC, Germantown, MD (US)

( * ) Notice: Subject to any disclaimer, the term of this patent is extended or adjusted under 35 U.S.C. 154(b) by 0 days.

(21) Appl. No.: 15/256,047

(22) Filed: Sep. 2, 2016

(65) Prior Publication Data
US 2016/0369337 A1    Dec. 22, 2016

Related U.S. Application Data

(63) Continuation of application No. 14/539,244, filed on Nov. 12, 2014, now Pat. No. 9,828,632, which is a
(Continued)

(51) Int. Cl.
*C12Q 1/6874*    (2018.01)
*G01N 21/64*    (2006.01)
(Continued)

(52) U.S. Cl.
CPC ....... *C12Q 1/6874* (2013.01); *G01N 21/6428* (2013.01); *G01N 21/6452* (2013.01); *G01N 21/6486* (2013.01); *G01N 21/05* (2013.01); *G01N 2021/0325* (2013.01); *G01N 2021/6421* (2013.01); *G01N 2021/6441* (2013.01); *G01N 2021/6471* (2013.01)

(58) Field of Classification Search
CPC .......... G01N 21/6428; G01N 21/6452; G01N 21/6486; G01N 21/05; G01N 2021/0325; G01N 2021/6421; G01N 2021/6441; G01N 2021/6471
USPC ........... 356/436, 456; 435/6.12, 6.1; 403/31
See application file for complete search history.

(56) References Cited

U.S. PATENT DOCUMENTS 5,313,264 A    5/1994 Ivarsson et al. ................ 356/73
6,097,025 A    8/2000 Modlin et al. ........... 250/227.11
(Continued)

FOREIGN PATENT DOCUMENTS

DE    000069511903 T2    4/2000
DE    000069634490 T2    3/2006
(Continued)

OTHER PUBLICATIONS

Bruchez, M., Jr. et al. (1998) "Semiconductor nanocrystals as fluorescent biological labels," *Science* 281(53S5), 2013-2016.
(Continued)

*Primary Examiner* — Isiaka O Akanbi
(74) *Attorney, Agent, or Firm* — Medlen & Carroll, LLP

(57) ABSTRACT

An imaging system for exciting and measuring fluorescence on or in samples comprising fluorescent materials (e.g. fluorescent labels, dyes or pigments). In one embodiment, a device is used to detect fluorescent labels on nucleic acid. In a preferred embodiment, the device is configured such that fluorescent labels in a plurality of different DNA templates are simultaneously detected.

16 Claims, 12 Drawing Sheets

Related U.S. Application Data continuation of application No. 12/704,842, filed on Feb. 12, 2010, now Pat. No. 8,940,481, which is a continuation of application No. 12/020,284, filed on Jan. 25, 2008, now abandoned.

(60) Provisional application No. 60/899,454, filed on Feb. 5, 2007.

(51) Int. Cl.
   *G01N 21/05* (2006.01)
   *G01N 21/03* (2006.01)

(56) References Cited

U.S. PATENT DOCUMENTS

| | | | |
|---|---|---|---|
| 6,545,758 B1 | 4/2003 | Sandstrom | 356/317 |
| 6,558,916 B2* | 5/2003 | Veerapandian | G01N 15/1404 |
| | | | 435/283.1 |
| 6,586,750 B2 | 7/2003 | Montagu et al. | 250/349 |
| 6,613,513 B1 | 9/2003 | Parce et al. | 435/6 |
| 6,856,390 B2 | 2/2005 | Nordman et al. | 356/344 |
| 7,147,362 B2 | 12/2006 | Caren et al. | 366/213 |
| 8,481,259 B2 | 7/2013 | Gordon et al. | 435/6.1 |
| 8,940,481 B2 | 1/2015 | Gordon et al. | 435/6.1 |
| 2001/0046050 A1* | 11/2001 | Hoyt | G01N 21/6428 |
| | | | 356/417 |
| 2004/0137604 A1 | 7/2004 | Goodman et al. | 435/286.5 |
| 2004/0174522 A1* | 9/2004 | Hagler | G01J 3/0229 |
| | | | 356/310 |
| 2005/0036142 A1* | 2/2005 | Oldham | B82Y 10/00 |
| | | | 356/344 |
| 2005/0042639 A1* | 2/2005 | Knapp | B01L 3/502761 |
| | | | 435/6.12 |
| 2005/0157299 A1* | 7/2005 | Heffelfinger | G01N 21/645 |
| | | | 356/417 |
| 2005/0202400 A1 | 9/2005 | Tsuji et al. | 435/29 |
| 2006/0012793 A1 | 1/2006 | Harris | 356/436 |
| 2006/0029267 A1 | 2/2006 | Frost et al. | 250/428 |
| 2006/0050277 A1* | 3/2006 | Ok | G01N 21/645 |
| | | | 356/417 |
| 2006/0127278 A1* | 6/2006 | Gast | G01N 21/648 |
| | | | 422/82.05 |
| 2006/0202133 A1* | 9/2006 | Ok | G01J 3/02 |
| | | | 250/458.1 |
| 2006/0228708 A1 | 10/2006 | Smilansky | 435/6 |
| 2006/0257993 A1 | 11/2006 | McDevitt et al. | 435/287.1 |
| 2006/0275893 A1 | 12/2006 | Ishii et al. | 435/287.2 |
| 2007/0131870 A1 | 6/2007 | Pang et al. | 250/428 |
| 2007/0247628 A1* | 10/2007 | Kivela | G01N 21/76 |
| | | | 356/432 |
| 2008/0117425 A1* | 5/2008 | Kain | C12Q 1/6837 |
| | | | 356/455 |
| 2008/0273918 A1* | 11/2008 | Linder | B01L 3/565 |
| | | | 403/31 |
| 2009/0116005 A1* | 5/2009 | Furuki | G01N 15/1425 |
| | | | 356/246 |

FOREIGN PATENT DOCUMENTS

| | | |
|---|---|---|
| DE | 102006058575 A1 | 6/2007 |
| DE | 602005002773 T2 | 7/2008 |
| DE | 102007021544 A1 | 11/2008 |
| EP | 0769159 A1 | 1/1996 |
| EP | 1529213 B1 | 5/2005 |
| EP | 1584692 A3 | 10/2007 |
| WO | WO 1997021090 | 6/1997 |
| WO | WO/1998/013683 | 4/1998 |
| WO | WO 2003078978 | 9/2003 |
| WO | WO/2003/100474 | 10/2004 |
| WO | WO 2008135566 | 11/2008 |

OTHER PUBLICATIONS

Chan, W. C. et al. (1998) "Quantum dot bioconjugates for ultrasensitive nonisotopic detection," *Science* 281(5385), 2016-2018.
International Search Report (ISR) for PCT/US08/01208 dated Jun. 25, 2008.

* cited by examiner

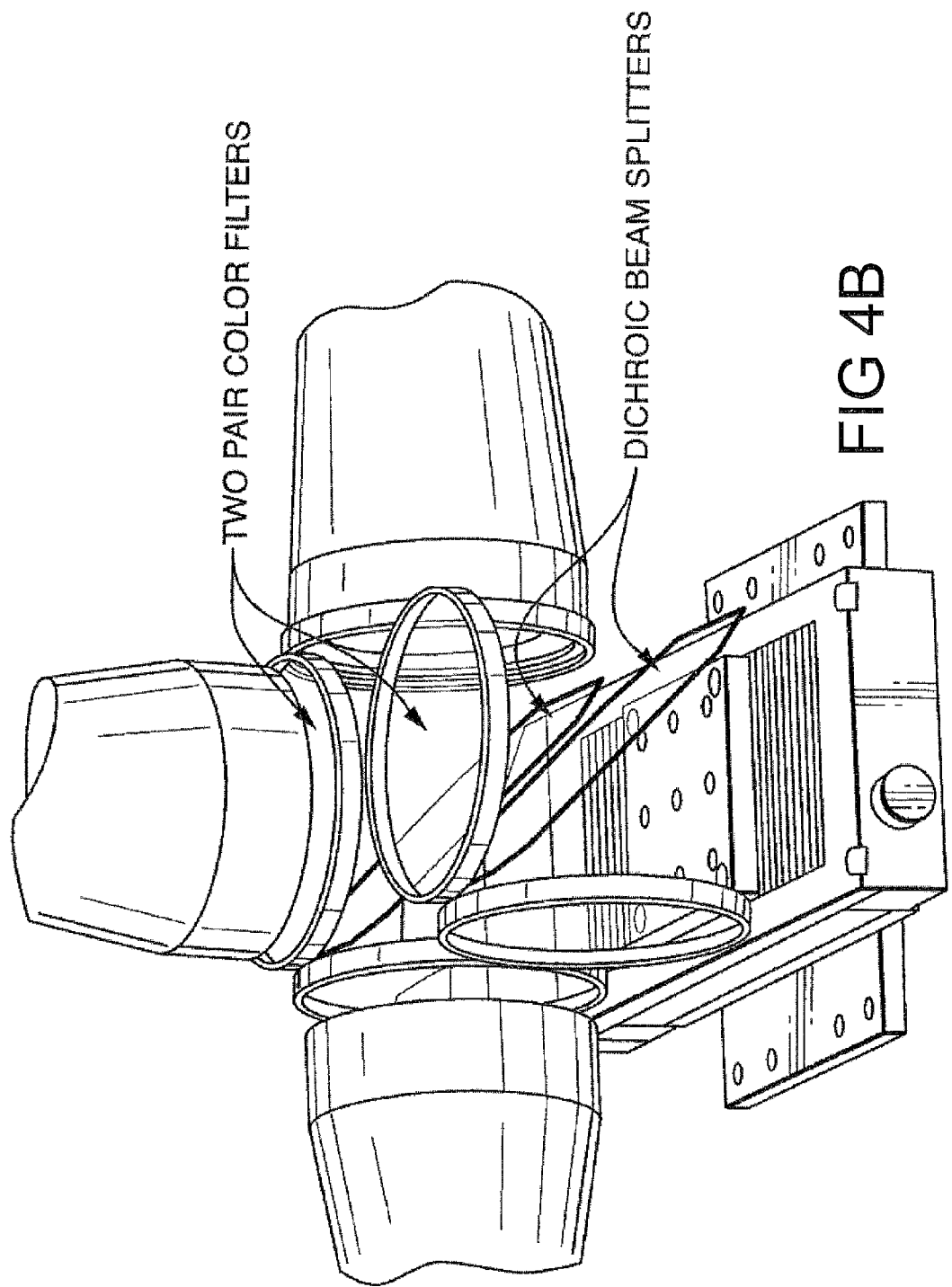

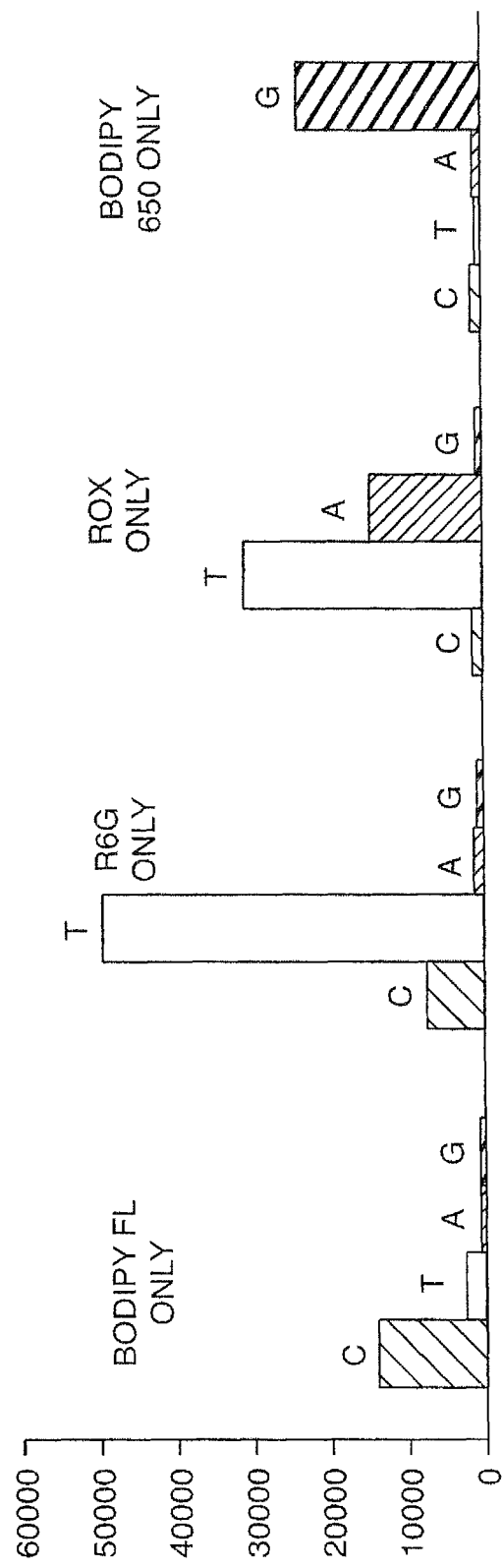

DETECTION DEVICE AND METHODS OF USE

FIELD OF INVENTION

The present invention is related to devices, methods for making devices and methods of using devices, including devices for detecting fluorescence. In one embodiment, the present invention contemplates an optical system, for exciting and measuring fluorescence on or in samples comprising fluorescent materials (e.g. fluorescent labels, dyes or pigments). In one embodiment, a device is used to detect fluorescent labels on nucleic acid. In a preferred embodiment, the device is configured such that fluorescent labels in a plurality of different DNA templates are simultaneously detected.

BACKGROUND

Scanning light microscopes have been known for several decades. Their functional principal is based on a light beam being concentrated to a small point of light (the first focal point) on a sample. The sample and this point of light are mutually moved in such a way that a specific area of the sample is scanned by the point of light. The light which penetrates the sample or is reflected by it and/or the fluorescence triggered on or in the sample during the scanning is therefore referred to as "light originating from the sample" and is measured by one or more photodetectors. An enlarged image is produced in that an original measurement point is assigned a specific area on an image of the sample. In principle, such a scanning light microscope therefore includes: a light source, such as a laser, which produces a light beam; a sample holder for holding the sample; an optic for producing a first focal point on the sample; an optical arrangement for imaging a second focal point using the light which shines through the sample and/or is reflected by the sample and/or which represents fluorescence triggered on or in the sample; a photodetector for measuring the intensity of the second focal point; and a scanning mechanism for mutual movement of the sample and first focal point.

The approach has a number of disadvantages. First, the small focal point means that only a very small portion of the sample can be addressed at one time. Second, the necessity for moving the light creates significant engineering issues and increased cost.

SUMMARY OF THE INVENTION

The present invention is related to devices, methods for making devices and methods of using devices, including devices for detecting fluorescence. In one embodiment, the present invention contemplates an optical system, for exciting and measuring fluorescence on or in samples comprising fluorescent materials (e.g. fluorescent labels, dyes or pigments). In one embodiment, a device is used to detect fluorescent labels on nucleic acid.

In a preferred embodiment, the device is configured such that fluorescent labels in a plurality of different DNA templates are simultaneously detected. In other words, rather than using a light source which creates a small focal point (such as a laser), the preferred light source of the present invention (preferably a non-lasing light source) illuminates a large area of a sample (e.g. at least 10% of the area defined by a conventional microscope slide, more preferably greater than 20% of the area defined by a conventional microscope slide, still more preferably, greater than 50% of the area defined by a conventional microscope slide, still more preferably, greater than 70% of the area defined by a conventional microscope slide). In another embodiment, the preferred light source of the present invention (preferably a non-lasing light source) illuminates a defined area of a chip (e.g. at least 10% of the area of the chip or 14.9×10 mm field of view). In still another embodiment, the preferred light source of the present invention illuminates a larger area of a chip (e.g. up to and including an image area of 22 mm×22 mm, and more preferably, 22 mm×66 mm). In a preferred embodiment, the system includes a light collection means such as a digital camera which is capable of capturing images (capable of recording 120 um features, and more preferably, 10 micron features or less).

With conventional devices, moreover, it is also difficult to perform concurrent measurements of a number of different fluorescent labels that may be present in a sample (or in different samples). There may be multiple fluorescent labeling agents that have different excitation and/or emission wavelengths. Existing fluorometers, however, do not facilitate such multiple-label experiments. Many fluorometers are designed for a single combination of excitation and emission wavelengths. By contrast, in a preferred embodiment, the imaging system of the present invention is designed for multiple excitation and emission wavelengths.

In one embodiment, the present invention contemplates an imaging system, comprising: a non-lasing light source configured such that the emitted light from said source illuminates (and preferably converges on) a flow cell (or portion thereof), said emitted light suitable for causing visible fluorescence of fluorescent compounds; a lens positioned to collect at least a portion of said visible fluorescence; and a light collection means (e.g. a light imaging/recording means such as a charge coupled device, a CMOS device, or other type of cameras) positioned such that said portion of said visible fluorescence collected by said lens passes through toward the light collection means. In one embodiment, the imaging system is conveniently contained within a housing (portions of which may be opaque or transparent). In one embodiment, the flow cell is mounted on a platform or other support structure. In another embodiment, the flow cell is attached to said housing (e.g. to a wall of the housing, or to a mount which is attached to the housing).

The various embodiments of the imaging system of the present invention can be complemented with hardware (e.g. a computer) or with software. Thus, in one embodiment, the imaging system further comprises a processor in communication with said light collection device (e.g. CCD or other digital camera), said processor capable of recording and (optionally) optimizing images from said system. With respect to optimizing, it may be practical and convenient to carry out optimization of the image noise in addition to the compensation of the brightness of the individual partial images. Corresponding methods for adaptive, noise-optimized filtering are known, for example, from the text of William A. Pratt entitled "Digital Imaging Processing", 1978, John Wiley & Sons, Inc., New York.

It is not intended that the present invention be limited by the arrangement of the imaging system. In one embodiment, the flow cell is on the bottom of the system and the other elements are positioned above it. In another embodiment, the flow cell is positioned to one side of the other elements, with the other elements positioned in a train or train-like manner. In one embodiment, the flow cell can be considered to occupy two spatial axes X and Y, with at least some of the other elements (e.g. the light source) positioned in the Z axis to illuminate the flow cell (or sample therein). On the other hand, the light source can be positioned differently, with the emitted light directed by mirrors into the Z axis. In one embodiment, it has been found convenient to position the flow cell such that the draining of the flow cell (e.g. the removal of fluids, such as solutions containing reagents, or wash buffers and the like) is achieved in part by gravity.

In a preferred embodiment, the flow cell is connected to a fluidics system, comprising various reagent and solution reservoirs in fluidic communication with said flow cell (e.g. via tubing). The fluidic system, in one embodiment, is pressurized and different reagents and solutions are introduced by controlled valving (described in more detail below). In some embodiment, said flow cell comprises one or more tubing connection ports.

It is not intended that the present invention be limited to the nature of the fluorescent compound(s) detected. The devices and systems of the present invention can be utilized with a variety of compounds, including but not limited to, dyes, inorganic molecules, multi-molecular mixtures of organic and/or inorganic molecules, crystals, heteropolymers, and the like. For example, CdSe—CdS core-shell nanocrystals enclosed in a silica shell may be easily derivatized for coupling to a biological molecule (Bruchez et al. (1998) Science, 281: 2013 2016). Similarly, highly fluorescent quantum dots (zinc sulfide-capped cadmium selenide) have been covalently coupled to biomolecules for use in ultrasensitive biological detection (Warren and Nie (1998) Science, 281: 2016 2018). Fluorescent oligonucleotides (primers or probes) containing base-linked or terminally-linked fluors and quenchers are well-known in the art. They can be obtained, for example, from Life Technologies (Gaithersburg, Md.), Sigma-Genosys (The Woodlands, Tex.), Genset Corp. (La Jolla, Calif.), or Synthetic Genetics (San Diego, Calif.). One of skill in the art will recognize that a large number of different fluorophores are available, including from commercial sources such as Molecular Probes, Eugene, Oreg. and other fluorophores are known to those of skill in the art. Useful fluorophores include: fluorescein, fluorescein isothiocyanate (FITC), carboxy tetrachloro fluorescein (TET), NHS-fluorescein, 5 and/or 6-carboxy fluorescein (FAM), 5- (or 6-) iodoacetamidofluorescein, 5-{[2(and 3)-5-(Acetylmercapto)-succinyl]amino} fluorescein (SAMSA-fluorescein), and other fluorescein derivatives, rhodamine, Lissamine rhodamine B sulfonyl chloride, Texas red sulfonyl chloride, 5 and/or 6 carboxy rhodamine (ROX) and other rhodamine derivatives, coumarin, 7-amino-methylcoumarin, 7-Amino-4-methylcoumarin-3-acetic acid (AMCA), and other coumarin derivatives, BODIPY™ fluorophores, Cascade Blue™ fluorophores such as 8-methoxypyrene-1,3,6-trisulfonic acid trisodium salt, Lucifer yellow fluorophores such as 3,6-Disulfonate-4-amino-naphthalimide, phycobiliproteins derivatives, Alexa fluor dyes (available from Molecular Probes, Eugene, Oreg.) and other fluorophores known to those of skill in the art. For a general listing of useful fluorophores, see also Hermanson, G. T., BIOCONJUGATE TECHNIQUES (Academic Press, San Diego, 1996). All such fluorescent materials are contemplated in the context of the present invention.

In the preferred embodiment of the imaging system of the present invention, said flow cell comprises an array of nucleic acid (e.g. the array is contained within the flow cell), at least a portion of said nucleic acid comprising fluorescent dyes (e.g. fluorescent labels covalently attached to a nucleotide incorporated in said nucleic acid). Preferably, said flow cell comprises means for introducing reagents in solution (such that biological reactions can take place on or in the array), said reagents selected from the group consisting of labeled nucleotides and enzymes (typically introduced in solution, such as buffers; the buffers also being useful alone for washing the array free of reactants).

It is not intended that the present invention be limited by the nature of the non-lasing light source. A variety of non-laser type light sources are contemplated, including but not limited to light emitting diodes (LEDs). In a preferred embodiment, the present invention contemplates a imaging system, wherein said non-lasing light source comprises a plurality of light emitting diodes. In a particularly preferred embodiment, said plurality of light emitting diodes comprises four different sets of light emitting diodes, each of which emit a different wavelength of light (e.g. 488 nm, 530 nm, 585 nm, and 615 nm). The light emitting diodes can be configured in an array (e.g. linear or circular) such that the emitting light illuminates (and preferably converges on) a sample (e.g. material on a microscope slide, an array, an array contained within a flow cell, a flow cell, etc.). It is not intended that the present invention be limited by the number of light emitting diodes. In one embodiment, the present invention contemplates the simple case where just four different LEDs are used (as distinct from four different sets of LEDs), each emitting a different wavelength. Even where four different sets are used, the present invention contemplates embodiments wherein there are equal numbers within each set, and embodiments where some or all sets have different numbers of light emitting diodes. Thus, for example, in a circular array of 20 LEDs, 7 may emit at one particular wavelength, while 3 may emit at another, with the remaining 10 comprising two sets of 5 LEDs, each set emitting at yet other wavelengths. Optionally, in order to further limit or narrow the wavelengths emitted by the LEDs, they may be combined with narrow bandpass filters placed between the LEDs and the sample (e.g. the flow cell containing the array on a chip). Further embodiments may optionally include additional elements used to shape the light (e.g. a shaping lens and/or collimating lens) from the light source.

In a preferred embodiment, the imaging system comprises filters positioned in front of the lens, within the lens, or between the lens and the light collection means. Preferably, the filters are optical bandpass filters which can be positioned in a linear or circular manner. In a particularly preferred embodiment of the imaging system described above, the system further comprises a filter wheel comprising a hub and a plurality of radially extending mounts, each of said mounts containing an optical bandpass filter. In a preferred embodiment, four such filters are employed, each selected for different preferred wavelengths. In one embodiment, four 50 mm interference filters are employed to allow the measurement of the fluorescent emissions of four different fluorophores.

The filters can be stationary or can be movable. In a preferred embodiment of the imaging system described above, the system further comprises a motor engaged (either directly or through transmission elements) with said hub of said filter wheel, wherein the motor is adapted to rotate said filter wheel to position any one of the plurality of filters between the light collection means (e.g. a charge coupled device) and the sample (e.g. the flow cell). Other means of limiting the bandwidth of light such as dichroic mirrors may also be used as a kind of filter.

In another embodiment, the present invention contemplates an imaging system, comprising: an array of light emitting diodes configured such that the emitted light illuminates (and preferably converges on) a sample comprising fluorescent materials, said emitted light suitable for causing visible fluorescence of fluorescent materials; a lens positioned to collect at least a portion of said visible fluorescence; and a charge coupled device positioned such that said portion of said visible fluorescence collected by said lens passes through toward the charge coupled device. In a preferred embodiment of the imaging system, said array of light emitting diodes comprises four different light emitting diode sets, each of which emit a different wavelength of light (e.g. 488 nm, 530 nm, 585 nm, and 615 nm). The light emitting diodes can be configured in an array (e.g. linear or circular) such that the emitting light illuminates (and preferably converges on) a sample (e.g. material on a microscope slide, an array, an array contained within a flow cell, a flow cell, etc.). It is not intended that the present invention be limited by the number of light emitting diodes. Even where four different sets are used, the present invention contemplates embodiments wherein there are equal numbers within each set, and embodiments where some or all sets have different numbers of light emitting diodes. Thus, for example, in a circular array of 20 LEDs, 7 may emit at one particular wavelength, while 3 may emit at another, with the remaining 10 comprising two sets of 5 LEDs, each set emitting at yet other wavelengths. Optionally, in order to further limit or narrow the wavelengths emitted by the LEDs, they may be combined with narrow bandpass filters placed between the LEDs and the sample (e.g. the flow cell containing the array on a chip). Further embodiments may optionally include additional elements used to shape the light (e.g. a shaping lens and/or collimating lens) from the light source.

In one embodiment of the imaging system, said sample comprises nucleic acid, at least a portion of said nucleic acid comprising fluorescent dyes. In a preferred embodiment, said sample is contained within a flow cell. In one embodiment, said flow cell comprises means for introducing reagents (typically in solution to said sample). In one embodiment, said reagents are selected from the group consisting of labeled nucleotides and enzymes (e.g. polymerases). As discussed above, in one embodiment, the flow cell is in fluidic communication with a fluidics system (via tubing and connection ports).

In a preferred embodiment, the imaging system comprises filters positioned in front of the lens, within the lens, or between the lens and the light collection means. Preferably, the filters are optical bandpass filters which can be positioned in a linear or circular manner. In a particularly preferred embodiment of the imaging system described above, the system further comprises a filter wheel comprising a hub and a plurality of radially extending mounts, each of said mounts containing an optical bandpass filter. In a preferred embodiment, four such filters are employed, each selected for different preferred wavelengths. In one embodiment, four 50 mm interference filters are employed to allow the measurement of the fluorescent emissions of four different fluorophores.

The filters can be stationary or can be movable. In a preferred embodiment of the imaging system described above, the system further comprises a motor engaged (either directly or through transmission elements) with said hub of said filter wheel, wherein the motor is adapted to rotate said filter wheel to position any one of the plurality of filters between the light collection means (e.g. a charge coupled device) and the sample (e.g. the flow cell).

In one embodiment, the present invention contemplates manufacturing an imaging system, comprising assembling: a non-lasing light source configured such that the emitted light from said source illuminates (and preferably converges on) a flow cell (or portion thereof), said emitted light suitable for causing visible fluorescence of fluorescent compounds; a lens positioned to collect at least a portion of said visible fluorescence; and a light collection means (e.g. a charge coupled device, a CMOS device, or other type of cameras) positioned such that said portion of said visible fluorescence collected by said lens passes through toward the light collection means. In one embodiment, said light source comprises LEDs (e.g. a circular array of LEDs).

In one embodiment, the present invention contemplates a method comprising: a) providing an imaging system, said imaging system comprising a non-lasing light source configured such that the emitted light from said source illuminates (and preferably converges on) a flow cell (or portion thereof) comprising an array of biomolecules, said emitted light suitable for causing visible fluorescence of fluorescent compounds; a lens positioned to collect at least a portion of said visible fluorescence; and a light collection means (e.g. a charge coupled device, a CMOS device, or other type of camera) positioned such that said portion of said visible fluorescence collected by said lens passes through toward the light collection means; b) introducing a solution into said flow cell, said solution comprising one or more fluorescent compounds, under conditions such that at least a portion of said fluorescent compounds attaches to at least a portion of said array of biomolecules, so as to create treated biomolecules, and c) imaging said treated biomolecules with said imaging system. In one embodiment of this method, the biomolecules comprises nucleic acid. In one embodiment of this method, the solution comprises oligonucleotides comprising fluorescent tags, wherein a portion of said oligonucleotides hybridize with a portion of said nucleic acid biomolecules of said array.

In another embodiment, said biomolecules comprise nucleic acid and said solution comprises fluorescently-labeled nucleotides and an enzyme capable of causing at least a portion of said nucleotides to be incorporated into at least a portion of said nucleic acid biomolecules of said array. In one embodiment, said nucleotides are BODIPY-labeled nucleotides. In another embodiment, a second solution is employed comprising one or more enzymes (or chemicals) capable of removing said fluorescent labels. In one embodiment, first and second solutions are used stepwise whereby labels are introduced, imaged, and subsequently removed (the cycle being repeated two times, more preferably 10 times or more).

In another embodiment, the present invention contemplates a method, comprising a) constructing a crosstalk matrix from measurement of pure dyes, b) inverting the matrix and c) using it to separate subsequent measurements using imaging system (such as the LED illumination-based detector system describe above). This crosstalk matrix can be constructed for a four color system (but is not limited to four colors).

DESCRIPTION OF THE FIGURES

FIG. 2A shows a three dimensional translucent view of a flow cell, comprising fluid tubing connections, cartridge heaters, and O-ring seal. FIG. 2B is a two dimensional drawing of a side view of a flow cell, showing an array or slide with spaced spots on the surface (representing positions for biomolecules and/or anchoring molecules), said array positioned in a fluid channel such that solutions of buffers and/or reagents can be introduced over the surface under conditions whereby reactions and/or washing can be achieved. The arrows show one preferred direction of fluid flow, with entrance and exit ports, as well as one preferred method of sealing (O-ring seal).

FIG. 4B shows a closer illustration of the three piece lens system, including the two pair color filters and dichroic beam splitters.

FIG. 5A shows the excitation and emission filter selection for the dye BODIPY FL. FIG. 5B shows the excitation and emission filter selection for the dye R6G. FIG. 5C shows the excitation and emission filter selection for the dye ROX. FIG. 5D shows the excitation and emission filter selection for the dye BODIPY 650.

FIGS. 6A-6B show the raw data (FIG. 6A) and crosstalk adjusted data (FIG. 6B) for four illustrative dyes.

DETAILED DESCRIPTION

The present invention contemplates a fluorescent detection system and a flow cell for processing biomolecules (e.g. nucleic acid samples) arrayed on a "chip" or other surface (e.g. microscope slide, etc.). The flow cell permits the user to perform biological reactions, including but not limited to, hybridization and sequencing of nucleic acids.

It is not intended that the present invention be limited to particular light sources. By way of example only, the system can employ ultra-bright LEDs (such as those available from Philips Lumileds Lighting Co., San Jose, Calif.) of different colors to excite dyes attached to the arrayed nucleic acids. These LEDs are more cost effective and longer life than conventionally used gas or solid state lasers. Other non-lasing sources of lights such as incandescent or fluorescent lamps may also be used.

Figure 1:
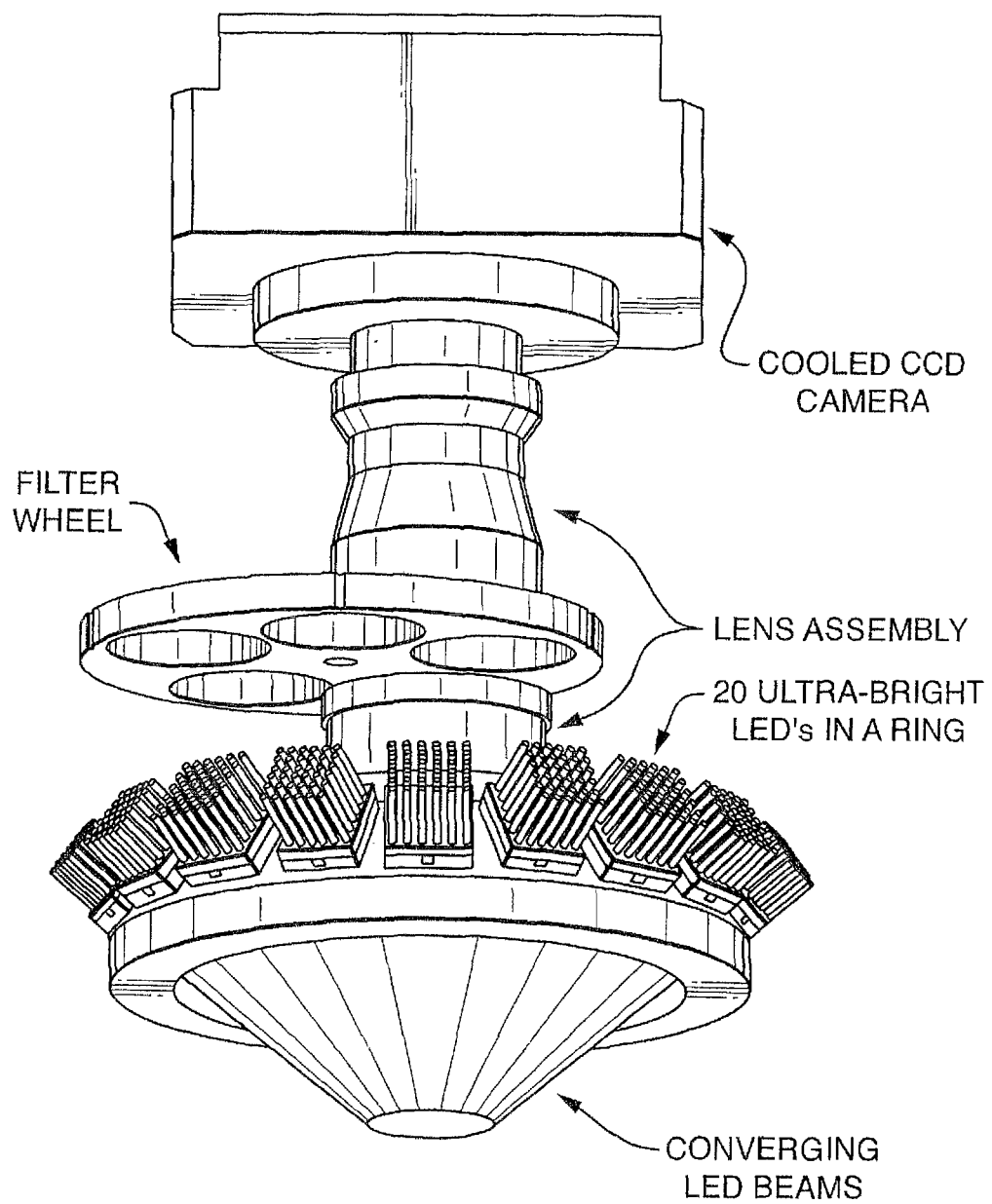
FIG. 1 schematically shows one embodiment of the imaging system of the present invention, said embodiment comprising a) a circular array of LEDs configured such that the emitted light converges on a region or platform (e.g. a position for a sample, flow cell, etc.) so as to excite fluorescence of fluorescent material, b) a lens assembly positioned above the region so as to capture at least a portion of said fluorescence, c) a filter wheel comprising bandpass filters, and d) light collection means (in this case a cooled CCD camera), wherein said filter wheel is positioned between the region where the light converges and the light collection means.

FIG. 1 shows a useful configuration of the LEDs, whereby the emitted light converges on a region or platform (e.g. suitable for positioning the flow cell or sample). However, linear arrays of LEDs can also be used.

It is not intended that the present invention be limited to particular light collection devices. By way of example only, the system may employ a high sensitivity CCD camera (such as those available from Roper Scientific, Inc., Photometric division, Tucson Ariz. or those available from Apogee Instruments, Roseville, Calif.) to image the fluorescent dyes and make measurements of their intensity. The CCD cameras may also be cooled to increase their sensitivity to low noise level signals. These may also be CMOS, vidicon or other types of electronic camera systems.

Since LED illumination light is not a collimated beam as from lasers, it is therefore an appropriate choice for imaging a larger area of many nucleic acid spots. To get sufficient light and therefore fluorescent signals over the larger area, the area seen by each pixel of the camera must be of sufficient size to allow enough fluorescent dye molecules to create a sufficient signal (for example, an Apogee U13 CCD available has 1.3 megapixels of 16 microns in size, while the Apogee U32 has 3.2 megapixels of 6.8 microns in size).

Figure 4A:
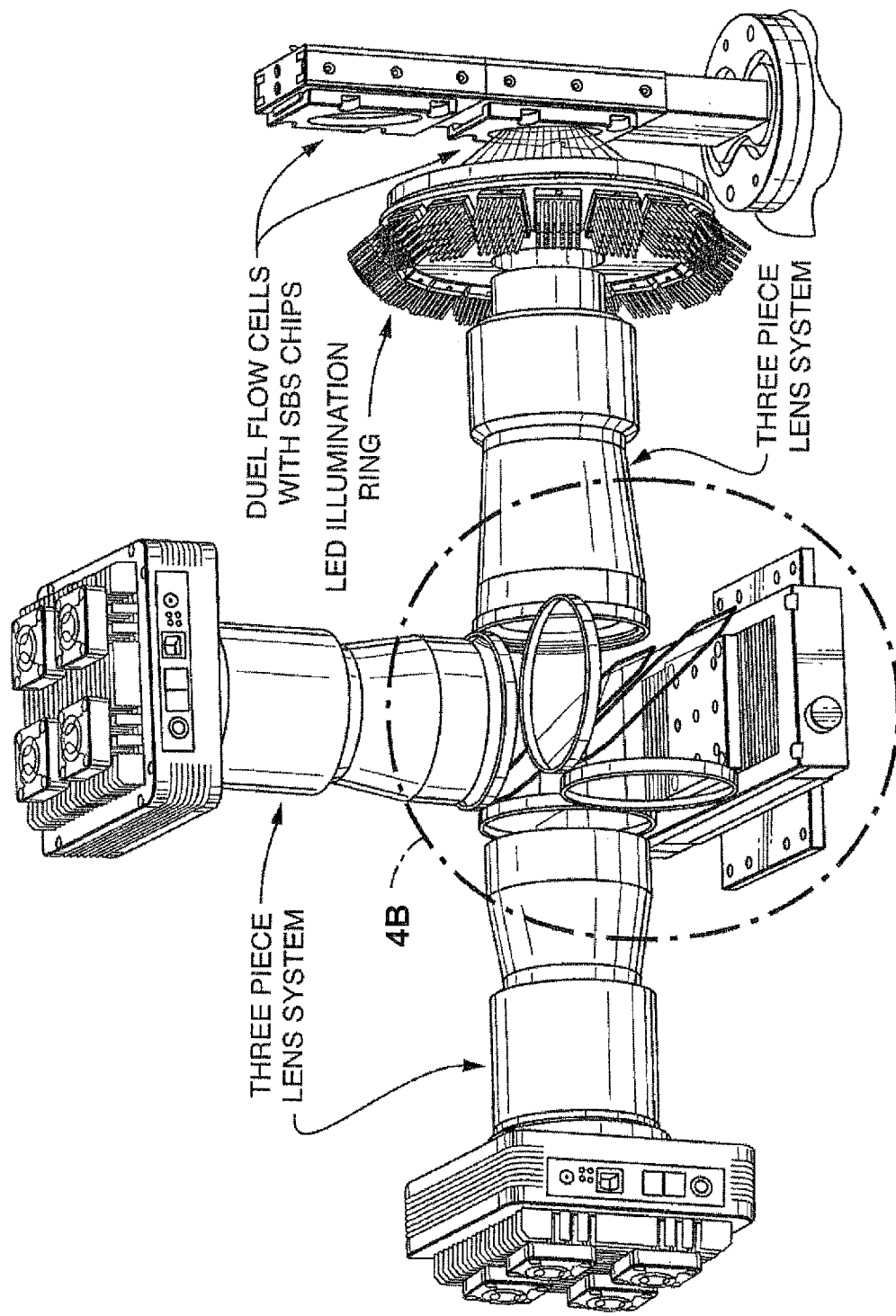
FIG. 4A schematically shows another embodiment of an imaging system, wherein two flow cells and two cameras are employed to increase capacity and efficiency (e.g. while one chip in a first flow cell is undergoing one or more reaction steps, a second chip in a second flow cell is being scanned and imaged).
Figure 5A:
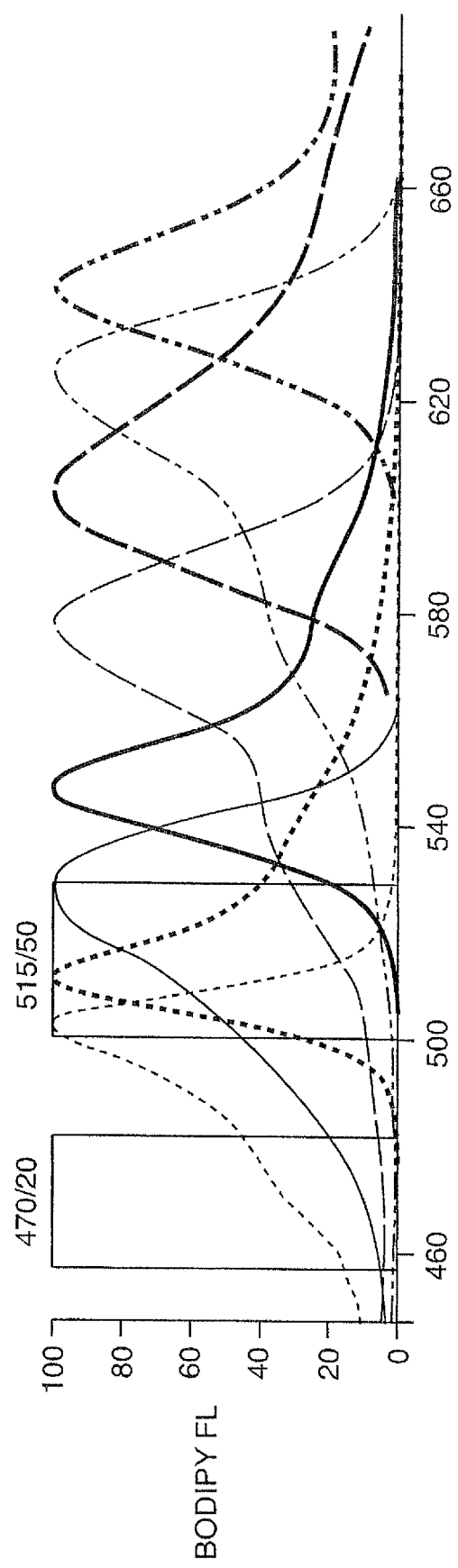
FIGS. 5A-5D show an illustrative excitation and emission filter selection (grey rectangles) for four illustrative dyes, relative to the dye's excitation (dashed) and emission (solid) spectra.
Figure 5B:
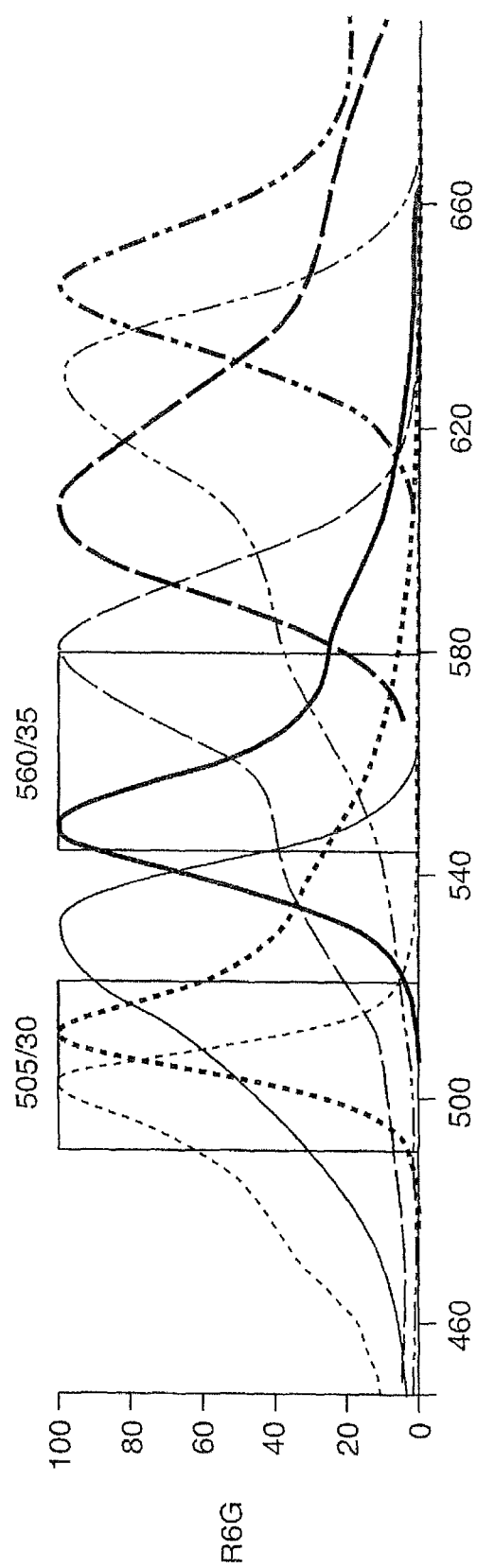
Figure 5C:
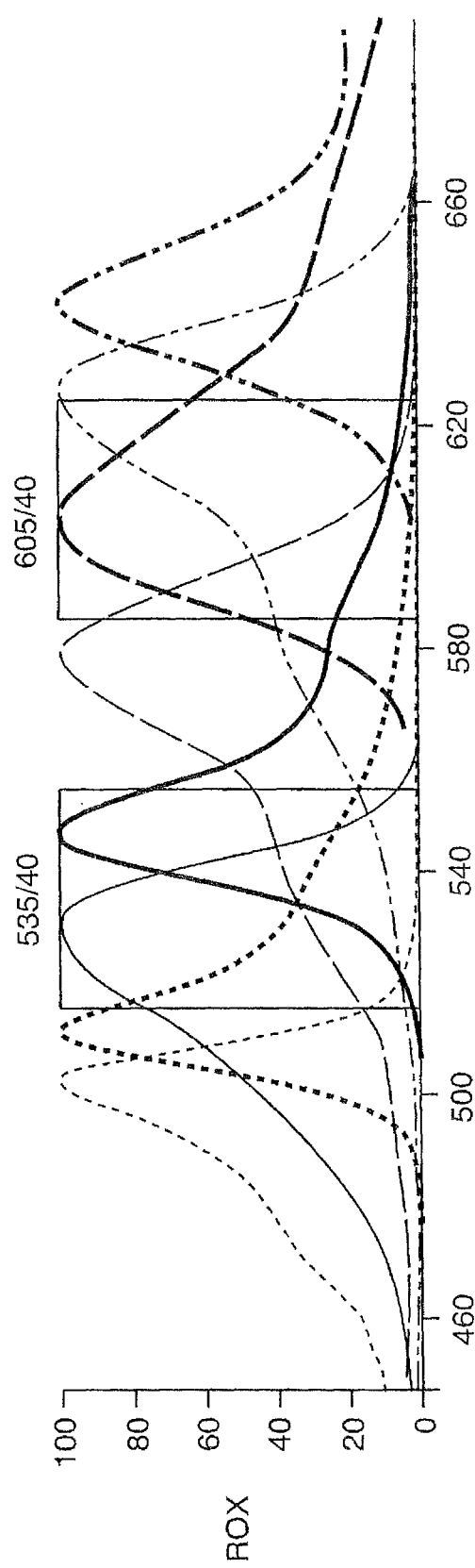
Figure 5D:
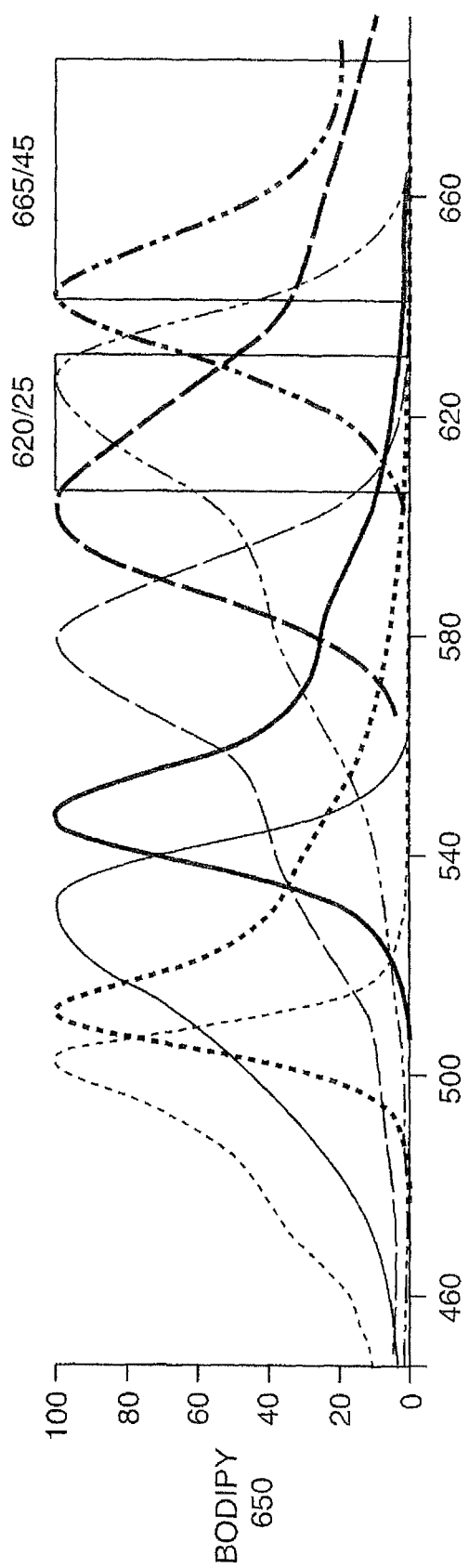

To increase capacity and efficiency, the present invention contemplates in one embodiment, a two flow cell system (e.g. while one chip in a first flow cell is undergoing one or more reaction steps, a second chip in a second flow cell is being scanned and imaged) with a single camera. In yet another embodiment of an imaging system, two flow cells and two cameras are employed (FIG. 4A and shown as a close up in FIG. 4B).

Figure 2A:
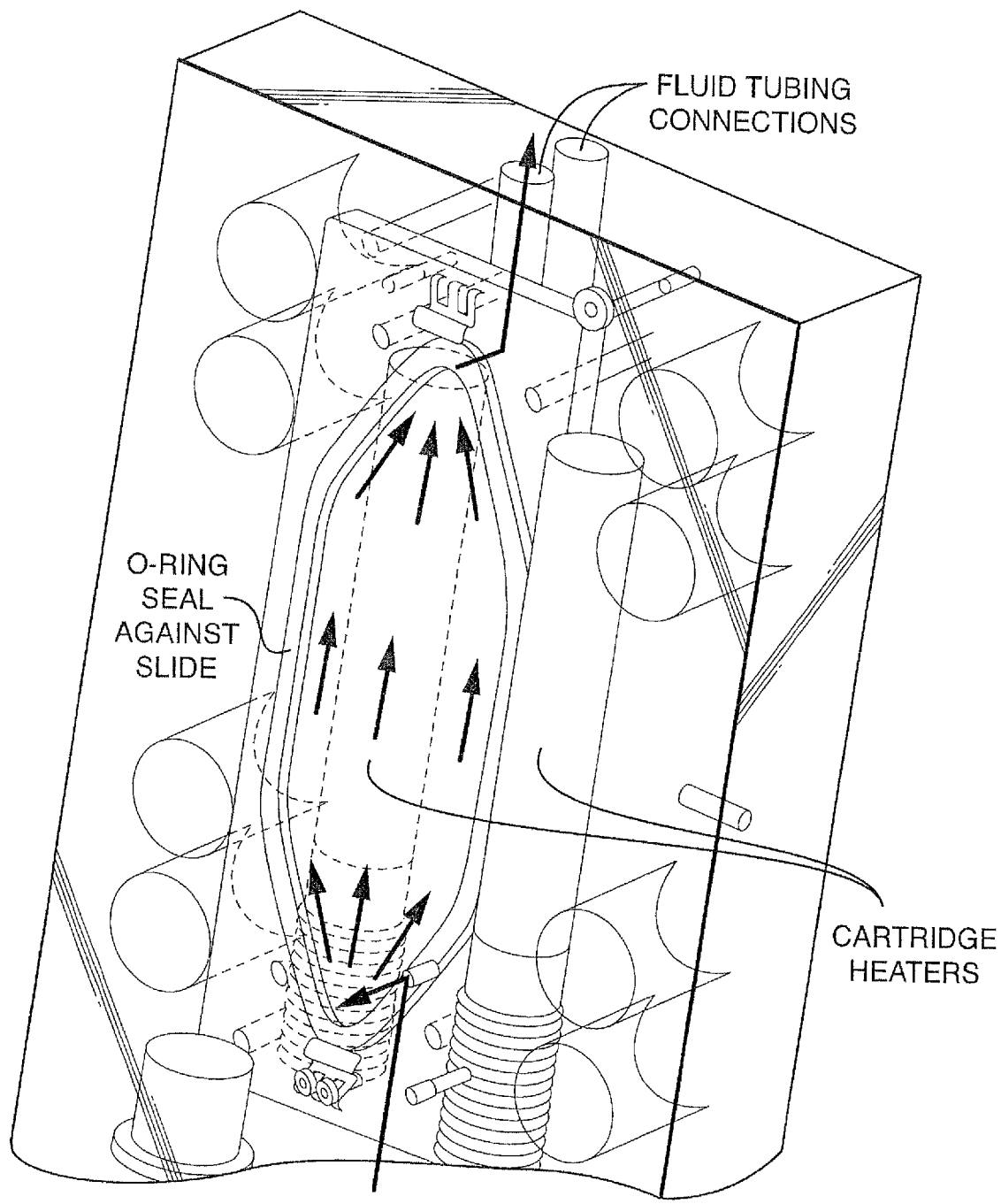
FIGS. 2A-B schematically show one embodiment of a flow cell.
Figure 2B:
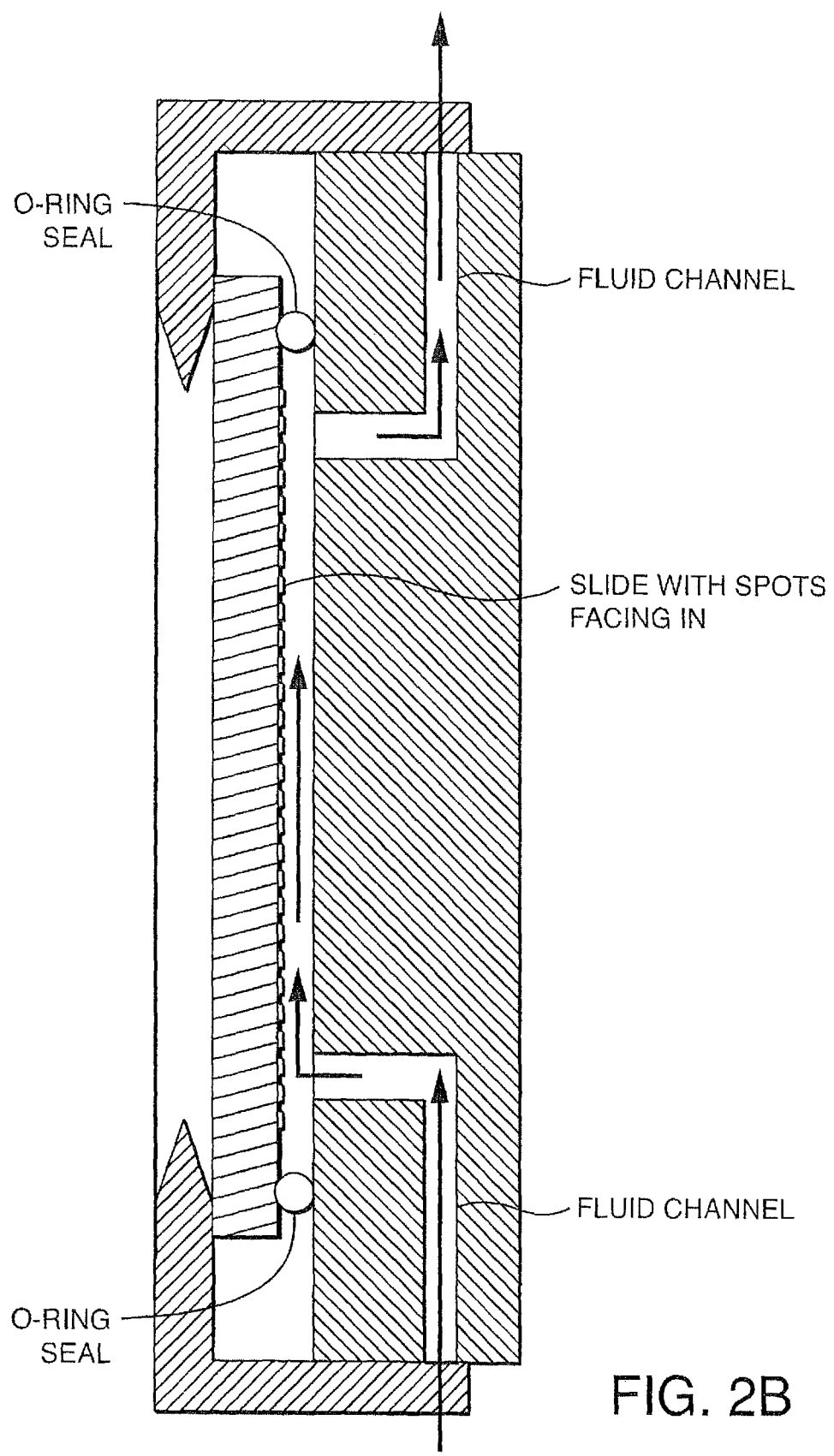

In one embodiment, the chip containing the array of nucleic acid spots is processed in a transparent flow cell incorporated within the instrument, which flows reagent past the spots and produces the signals required for sequencing (see FIGS. 2A and 2B). In a preferred embodiment, the chip remains in the flow cell while it is imaged by the LED detector. The flow cell and associated reagents adds the nucleic acids, enzymes, buffers, etc. that are required to produce the fluorescent signals required for each sequencing step, then the flow cell delivered the required reagents to remove the fluorescent signals in preparation for the next cycle. Measurement by the detector occurs between these two steps. In order for reactions to take place, the flow channels need to be of sufficient dimensions. For example, the channel by the array should be at least 0.1 mm in depth (more preferably 0.5 mm in depth) and the volume formed by the chip, the block and the seal should be at least 100 microliters in volume (more preferably, between 100 and 700 microliters, and still more preferably, between 150 and 300 microliters, e.g. 200 microliters, in volume).

The flow cell is preferably motionless (i.e. not moved during reactions or imaging). On the other hand, the flow cell can readily be mounted on a rotary or one or more linear stages, permitting movement. For example, in a two flow cell embodiment, the two flow cells may move up and down (or side to side) across the imaging system. Movement may be desired where additional processes are desired (e.g. where exposure to UV light is desired for photochemical reactions within the flow cell, such as removal of photocleavable fluorescent labels), when multiple flow cells share a single camera, or when the field of view of the detection system is smaller than the desired area to be measured on the flow cell. The detector system may also be moved instead of the flow cell.

Figure 3:
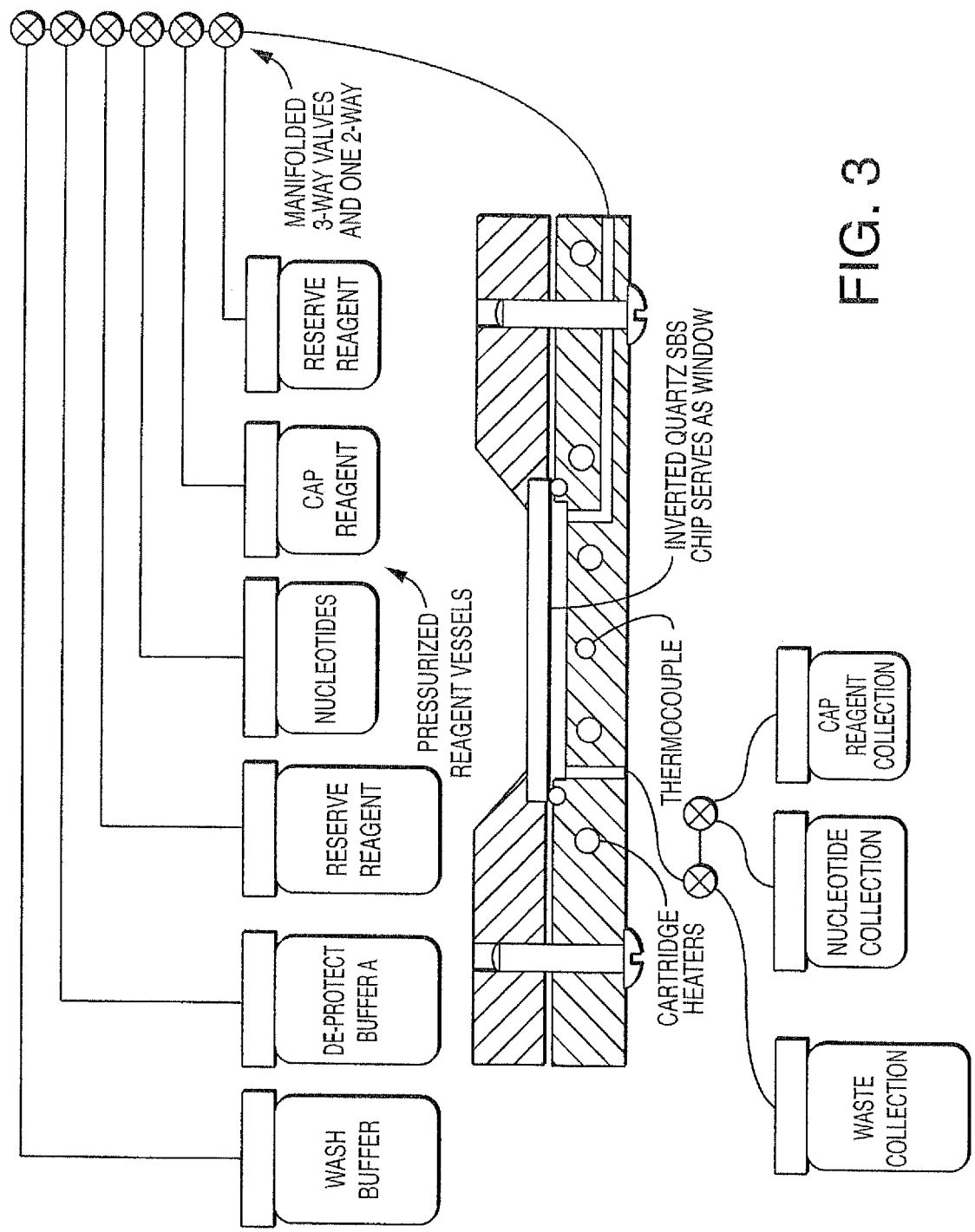
FIG. 3 schematically shows one embodiment of a fluidics system, comprising a variety of illustrative reagent and buffer reservoirs in communication (via tubing or other channeling into a manifold comprising valves) with one embodiment of a flow cell (comprising a side entrance port and one or more heaters), wherein the array or chip is inverted and the exit port is on the bottom, thereby permitting the fluid channel to be drained at least in part by gravity so that waste can be readily collected into a reservoir.

The flow cell is preferably in fluid communication with a fluidics system (see illustrative system shown in FIG. 3. In one embodiment, each bottle is pressurized with a small positive gas pressure. Opening the appropriate valve allows reagent to flow from the source bottle through the flow cell to the appropriate collection vessel(s). In one embodiment, the nucleotides and polymerase solutions will be recovered in a separate collection bottle for re-use in a subsequent cycle. In one embodiment, hazardous waste will be recovered in a separate collection bottle. The bottle and valve configuration allow the wash fluid to flush the entire valve train for the system as well as the flow cell. In one embodiment, the process steps comprise: 1) flushing the system with wash reagent, 2) introducing nucleotides (e.g. flowing a nucleotide cocktail) and polymerase, 3) flushing the system with wash reagent, 4) introducing de-blocking reagent (enzyme or compounds capable of removing protective groups in order to permit nucleic acid extension by a polymerase), 5) image, 6) introduce label removing reagent (enzyme or compounds capable of removing fluorescent labels), and 7) flushing the system with wash reagent.

The system can be made to include a user interface system. The Labview (National Instruments, Austin, Tex.) system is available and provides relatively simply software for computer controlled systems. Galil Motion Control (Rocklin, Calif.) provides motion control systems that can be interfaced to control the instrument.

Example

Method for Removing Crosstalk Between Detected Fluorescent Signals for a Multicolor System Previous sequencing systems utilizing lasers have attempted to minimize the number of lasers in order to reduce costs (for example ABI Prism sequencers). For a four color detection system using LEDs, the light sources are fairly inexpensive and it is desirable to have four separate color light sources in order to reduce crosstalk between colors as follows.

To determine actual fluorescent intensities for the four colors, A, B, C and D from measured detector outputs, $M_A$, $M_B$, $M_C$, $M_D$ in corresponding channels, you need to know all of the crosstalk factors: $R_{AB}$, $R_{BA}$, $R_{BC}$, $R_{CB}$, $R_{CD}$, $R_{DC}$. Six crosstalk factors are used for illustrative purposes. There may be more or fewer factors which may be incorporated into the analysis.

For example, $R_{AB}$ is the ratio between the portion of the signal in the A channel coming from the B dye and the actual intensity of the B dye. If for instance $R_{AB}$ is 20%, then the A channel will have an additional signal equal to 0.2 times the actual B dye intensity in the B channel. Thus for channel B, the observed measurement, $M_B$, is the direct measurement of B and the two contributions from the adjacent channels (if any):

$$M_B = B + R_{BA}A + R_{BC}C \quad (1)$$

For the four channels, this may be written in matrix form:

$$\begin{bmatrix} M_A \\ M_B \\ M_C \\ M_D \end{bmatrix} = K \begin{bmatrix} A \\ B \\ C \\ D \end{bmatrix} \text{ where } K = \begin{bmatrix} 1 & R_{AB} & 0 & 0 \\ R_{BA} & 1 & R_{BC} & 0 \\ 0 & R_{CB} & 1 & R_{CD} \\ 0 & 0 & R_{DC} & 1 \end{bmatrix}. \quad (2)$$

Figure 6B:
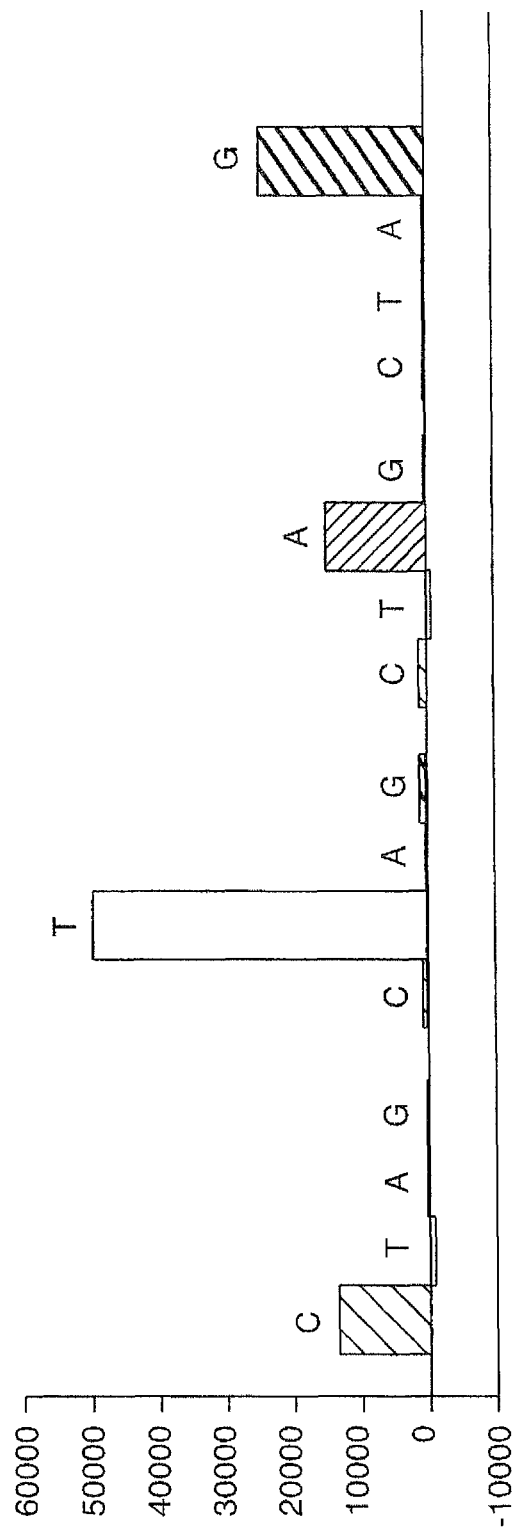

Each of the six crosstalk factors may be determined through a simple experiment with pure dyes. Some may be zero and they might vary with intensity, so we may need a table of a number of values for each depending on the measured intensity range. We want to solve for the actual fluorescent signals, A, B, C and D given the detector measurements, $M_A$, $M_B$, $M_C$, $M_D$. Thus, we want to solve the above matrix equation (2). This is:

$$\begin{bmatrix} A \\ B \\ C \\ D \end{bmatrix} = K^{-1} \begin{bmatrix} M_A \\ M_B \\ M_C \\ M_D \end{bmatrix} \quad (3)$$

where $K^{-1}$ is the inverse of matrix K. Although this may be written out in terms of the six crosstalk factors, it is somewhat complex and is best performed by plugging in the numbers and letting the computer take the inverse. FIG. 6 shows the raw data (6A) and crosstalk adjusted data (6B) for four illustrative dyes.

The invention claimed is:

1. A method comprising:
   a) providing an imaging system, said imaging system comprising
      i) a non-lasing light source, emitting different wavelengths of light, configured such that the emitted visible light from said source illuminates a portion of a flow cell,
      ii) said flow cell comprising an array of biomolecules on a surface, wherein said emitted light illuminates said surface, wherein said array faces inwardly so that reagents introduced in solution can contact said biomolecules, wherein said flow cell comprises a fluidic connection to at least one reagent bottle wherein said at least one reagent bottle is under a positive pressure,
      iii) a lens positioned to collect a portion of a visible fluorescence; and
      iv) a camera;
   b) introducing a solution via said fluidic connection into said flow cell, said solution comprising a plurality of fluorescent compounds having different excitation and emission wavelengths, under conditions such that a portion of said fluorescent compounds attaches to a portion of said array of biomolecules, so as to create treated biomolecules,
   c) illuminating said flow cell with said light source emitting different wavelengths of light, wherein said emitted visible light from said source converges on said fluorescent compounds, and
   d) concurrently imaging said treated biomolecules illuminated with said light source emitting different wavelengths of light with said imaging system.

2. The method of claim 1, wherein said flow cell is transparent.

3. The method of claim 1, wherein said array of biomolecules comprises an array of nucleic acid.

4. The method of claim 1, wherein said fluorescent compounds comprise labeled nucleotides.

5. The method of claim 4, wherein said solution of step b) further comprises polymerase.

6. The method of claim 1, further comprising, prior to step d) removing said solution from said flow cell.

7. The method of claim 6, wherein said removing is achieved in part by gravity.

8. The method of claim 1, wherein said flow cell is connected to a fluidics system.

9. The method of claim 1, wherein said solution is under positive pressure and is introduced at step b) by controlled valving.

10. A method comprising:
a) providing an imaging system, said imaging system comprising
   i) first, second, third and fourth non-lasing light sources, each source emitting a different wavelength of visible light and configured such that the emitted light from said source illuminates a portion of a flow cell,
   ii) said flow cell comprising an array of biomolecules positioned so that reagents introduced in solution can contact said biomolecules, wherein said flow cell comprises a fluidic connection to at least one reagent bottle wherein said at least one reagent bottle is under a positive pressure,
   iii) a lens positioned to collect a portion of a visible fluorescence; and
   iv) a camera;
b) introducing a solution via said fluidic connection into said flow cell, said solution comprising a plurality of fluorescent compounds having different excitation and emission wavelengths, under conditions such that a portion of said fluorescent compounds attaches to a portion of said array of biomolecules, so as to create treated biomolecules,
c) illuminating said flow cell with said light source emitting different wavelengths of light, and
d) concurrently imaging said treated biomolecules illuminated with said light source emitting different wavelengths of light with said imaging system.

11. The method of claim 10, wherein said light sources are light emitting diodes.

12. The method of claim 10, wherein two of said four wavelengths comprise 488 nm and 530 nm.

13. The method of claim 10, wherein said flow cell comprises one or more flow channels, and said array of biomolecules is positioned in a channel under conditions such that said array contacts said solution upon said introducing of said solution of step (b).

14. The method of claim 12, wherein one of said one or more flow channels has a first surface and a second surface, and wherein said array is positioned on said first surface.

15. A method comprising:
a) providing an imaging system, said imaging system comprising
   i) first and second non-lasing light sources, each source emitting different wavelengths of visible light and configured such that the emitted light from said source illuminates a portion of a flow cell,
   ii) said flow cell comprising biomolecules positioned so that reagents introduced in solution can contact said biomolecules, wherein said array of biomolecules comprises an array of nucleic acid, wherein said flow cell comprises a fluidic connection to at least one reagent bottle wherein said at least one reagent bottle is under a positive pressure,
   iii) a lens positioned to collect a portion of a visible fluorescence; and
   iv) a camera;
b) introducing a solution via said fluidic connection into said flow cell, said solution comprising a plurality of fluorescent compounds having different excitation and emission wavelengths, under conditions such that a portion of said fluorescent compounds attaches to a portion of said biomolecules, so as to create treated biomolecules,
c) illuminating said flow cell with said light source emitting different wavelengths of light, wherein said emitted visible light from said source converges on said fluorescent compounds, and
d) concurrently imaging said treated biomolecules illuminated with said light source emitting different wavelengths of light with said imaging system.

16. The method of claim 15, wherein said light sources are light emitting diodes.

* * * * *